(12) United States Patent
Hofmeier et al.

(10) Patent No.: US 9,040,697 B2
(45) Date of Patent: May 26, 2015

(54) PROCESS FOR THE PRODUCTION OF MOXONIDINE

(71) Applicant: Arevipharma GmbH, Radebeul (DE)

(72) Inventors: Harald Hofmeier, Dresden (DE); Michael Limmert, Dresden (DE); Heike Heydemüller, Dresden (DE); Helge Hartenhauer, Dresden (DE)

(73) Assignee: AREVIPHARMA GmbH, Radebeul (DE)

( * ) Notice: Subject to any disclaimer, the term of this patent is extended or adjusted under 35 U.S.C. 154(b) by 0 days.

(21) Appl. No.: 14/173,688

(22) Filed: Feb. 5, 2014

(65) Prior Publication Data

US 2014/0228383 A1    Aug. 14, 2014

Related U.S. Application Data

(60) Provisional application No. 61/762,344, filed on Feb. 8, 2013.

(30) Foreign Application Priority Data

Feb. 8, 2013    (EP) .................... 13154635

(51) Int. Cl.
C07D 239/24    (2006.01)
C07D 403/12    (2006.01)
A61K 31/506    (2006.01)

(52) U.S. Cl.
CPC ............ *C07D 403/12* (2013.01); *A61K 31/506* (2013.01)

(58) Field of Classification Search
CPC ........................... C07D 239/24; C07D 403/12
USPC .......................................... 544/298, 315, 316
See application file for complete search history.

(56) References Cited

U.S. PATENT DOCUMENTS 4,323,570 A    4/1982  Stenzel et al.
4,938,793 A *  7/1990  Watson et al. ............... 504/239
5,684,156 A   11/1997  Pierce et al.

FOREIGN PATENT DOCUMENTS

| CZ | 294 649 B6 | 5/2004 |
| CZ | 20040218 A3 | 5/2004 |
| DE | 28 49 537 A1 | 5/1980 |
| DE | 29 37 023 A1 | 4/1981 |
| EP | 1 873 152 A1 | 1/2008 |
| EP | 1 894 926 A1 | 3/2008 |
| EP | 1 894 927 A1 | 3/2008 |
| EP | 1 981 498 A2 | 10/2008 |
| EP | 1 982 983 A1 | 10/2008 |
| WO | WO 2007/090720 A2 | 8/2007 |
| WO | WO 2008/073125 A1 | 6/2008 |

* cited by examiner

*Primary Examiner* — Golam M M Shameem
(74) *Attorney, Agent, or Firm* — Arent Fox LLP

(57) ABSTRACT 4,6-dichloro-2-methyl-5-(1-acyl-2-imidazolin-2-yl)-aminopyrimidine is reacted with methanol in the presence of a non-ionic organic base, and moxonidine is obtained directly from the reaction mixture.

14 Claims, No Drawings

PROCESS FOR THE PRODUCTION OF MOXONIDINE

CROSS-REFERENCE TO RELATED APPLICATION

This application claims the benefit of U.S. Patent Provisional Application No. 61/762,344 filed Feb. 8, 2013, which claims the benefit of priority to EP 13154635.0 filed Feb. 8, 2013, the entire specification, claims and drawings of which are incorporated herewith by reference.

FIELD OF THE INVENTION

The present invention relates to organic synthesis, in particular to a novel process for the production of Moxonidine.

BACKGROUND OF THE INVENTION

Moxonidine having the structural formula I

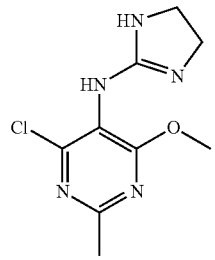

is a new generation centrally acting antihypertensive drug licensed for the treatment of mild to moderate essential hypertension. It may have a role when thiazides, beta-blockers, ACE inhibitors and calcium channel blockers are not appropriate or have failed to control blood pressure. In addition, it demonstrates favourable effects on parameters of the insulin resistance syndrome, apparently independent of blood pressure reduction. It is a selective agonist at the imidazoline receptor subtype 1 (I1). In addition, moxonidine may also promote sodium excretion, improve insulin resistance and glucose tolerance and protect against hypertensive target organ damage, such as kidney disease and cardiac hypertrophy.

Moxonidine was first disclosed by DE2849537A filed in 1979. Nowadays the compound is available as generic drug. The compound was synthesized by reaction of a 4,6-chloro-5-aminopyrimidine component III with 1-acyl-imidazolidin-2-one IV to intermediate II (R=Acetyl: "DMAIA" (IIa)), followed by substitution of one chloro group by a methoxy group using sodium methoxide/methylate (DE2937023A1, U.S. Pat. No. 4,323,570). EP 1982983A describes an optimized process using sodium methoxide/methylate (NaOMe).

The synthesis of Moxonidine according to original route is shown in scheme 1 below. Pyrimidine systems, in general, can be constructed by conversion of a nitrile to a "Pinner salt", subsequent ammonialysis and finally condensation with a malonic ester, as shown in scheme 2 below.

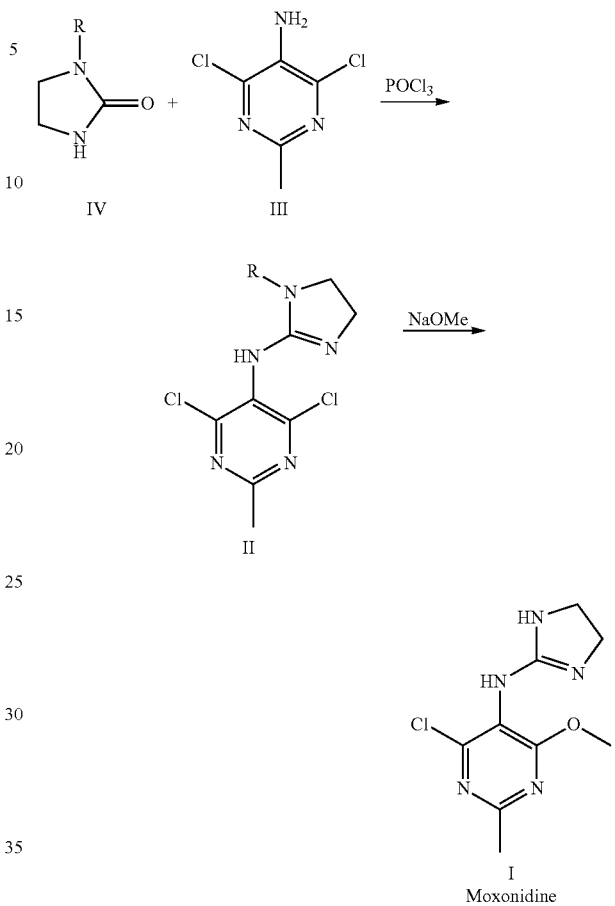

Scheme 1: Conventional synthesis of moxonidine for R = C(O)CH$_3$; 4,6-dichloro-2-methyl-5-(1-acetyl-2-imidazolin-2-yl)-aminopyrimidine (DMAIA, IIa)

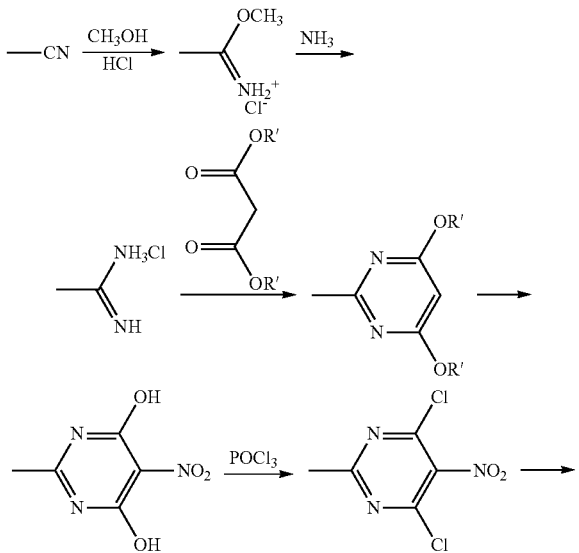

Scheme 2: Synthesis of the pyrimidine system via Pinner salt.

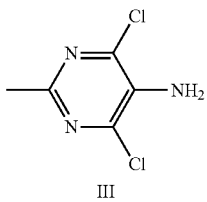

III

Many process related improvements followed, particularly in the field of the base employed in the chloro-methoxy substitution step and the reaction conditions in this step. In order to avoid the disadvantageous use of methoxide, EP1873151A for example describes various alkali hydroxides and (bi)carbonates as well as different reaction conditions regarding equivalents, temperature and time. The reactions were performed in methanol and the crude product isolated after addition of water to the reaction mixture, which is necessary to dissolve inorganic salts that are inevitable when using inorganic base. CZ 294649B6 describes the process in presence of $K_2CO_3$ or $NaHCO_3$. WO2008073125A1 describes improved conditions for the first step (coupling) together with an impurity arising from this step.

Some other synthetic routes to moxonidine are also known, for example via thioureas and thioisocyanates (DE2849537A, U.S. Pat. No. 5,684,156A, EP1981498A, WO2007090720A2).

Usually, these conditions suffer from the impurity control and bear the risk of inorganic residues in the product. Therefore, an additional purification step is usually required. In EP1873152A, recrystallization in high-boiling solvents was performed. EP1894927A claims the formation of salts of moxonidine (with organic or inorganic acids). Moreover, these salts were utilized for purification of Moxonidine by reaction with a base to liberate the free Moxonidine. EP1894926A1 describes the preparation (crystallization, precipitation) and characterization of three crystalline forms. In most cases moxonidine is prepared from IIa by applying an inorganic base in methanol. Drawbacks of those processes are difficult control of the impurity profile, because of a usually heterogeneous reaction mixture, and the risk of elevated amounts of inorganic impurities in the final product.

It is therefore an object of the present invention to provide a more simple and reliable process for the production of moxonidine.

SUMMARY OF THE INVENTION

The present invention provides a novel process for the production of moxonidine and its pharmaceutically acceptable salts. Preferred embodiments are set forth below.

It was surprisingly discovered that, when preparing moxonidine from the readily available precursors of formula II by the use of methanol and a non-ionic organic base, product can be precipitated or crystallized from the homogeneous reaction mixture without the need for an additional purification step: the crude product already meets pharmacopoeial requirements (cf. European Pharmacopeia, version 7.0). Due to the advantageous reaction conditions the process is very robust and more reproducible than those as described in the prior art by allowing for an outstanding reproducibility and control of the impurity profile.

One of the further advantages of the present invention is the omission of inorganic bases, thereby eliminating issues of inorganic residues in the final product. It is another advantage that aqueous media and organic co-solvents can preferably be omitted, rendering the process simple.

In conclusion the present invention provides for a simpler, shorter, however more reliable and thus economically more viable process.

Various aspects, advantageous features and preferred embodiments of the present invention as summarized in the following items, respectively alone or in combination, contribute to solving the object of the invention:

(1) A process for the synthesis of moxonidine of formula I

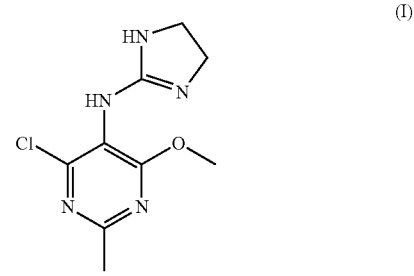 [SMILES: COc1nc(C)nc(Cl)c1NC1=NCCN1]

or a pharmaceutically acceptable salt thereof, the process comprising the steps of: reacting a compound of formula II

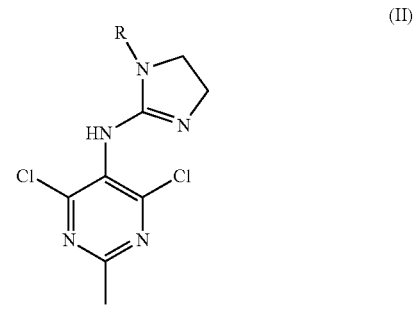

wherein R denotes an acyl group, such as formyl, acetyl, propionyl, or butyryl groups
optionally substituted, e.g. by a phenyl group, preferably R is acetyl,
with methanol in the presence of a non-ionic, organic base; and
obtaining moxonidine I from the reaction mixture.

(2) The process according to item (1), wherein the reaction is performed in a medium which is essentially non-aqueous, preferably the reaction is performed in an organic solvent.

(3) The process according to items (1) or (2), wherein methanol is the only reaction medium, and without addition of water during or after the reaction process.

(4) The process according to any one of the preceding items, wherein 4,6-dichloro-2-methyl-5-(1-acetyl-2-imidazolin-2-yl)-aminopyrimidine (DMAIA, wherein R is acetyl; compound of formula IIa) is reacted with methanol.

(5) The process according to any one of the preceding items, wherein the organic base is selected from organic nitrogen bases.

(6) The process according to item (5), wherein the organic nitrogen base is selected from a group comprising: guanidines, preferably N,N,N',N'-tetramethylguanidine or N-methyl-hexahydro-pyrimido-pyrimidine; amidines, preferably 1,5-diazabicyclo[4.3.0]non-5-ene (DBN) and 1,8-diazabicyclo[5.4.0]undec-7-ene (DBU)), and amines.

(7) The process according to items (5) or (6), wherein the organic nitrogen base is DBN or DBU, more preferably DBU.

(8) The process according to any one of the preceding items, wherein 1.0-2.0 molar equivalents, preferably 1.4 to 1.5 molar equivalents of organic base, relative to the compound of formula II.

(9) The process according to any one of the preceding items, wherein the volume ratio is adjusted to 20-40 ml of methanol per g of compound of formula II.

(10) The process according to any one of the preceding items, wherein the reaction is carried out in the presence of activated charcoal.

(11) The process according to any one of the preceding items, wherein, prior to isolation of moxonidine from the reaction mixture, an organic acid, preferably acetic acid, is added.

(12) The process according to any one of the preceding items, wherein moxonidine is isolated from the reaction mixture by precipitation or crystallization.

(13) The process according to any one of the preceding items, wherein prior to the isolation of moxonidine from the reaction mixture the reaction mixture is concentrated, optionally after an initial crystallization period, and finally moxonidine is isolated.

(14) A process for preparing a pharmaceutical composition comprising moxonidine of formula I or a pharmaceutically acceptable salt thereof,

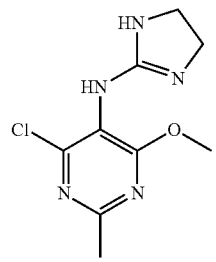

(I)

the process comprising:
carrying out a process according to any one of items (1) to (13) for preparing said moxonidine of formula I or a pharmaceutically acceptable salt thereof, and
mixing the prepared moxonidine compound of formula I or a pharmaceutically acceptable salt thereof with at least one pharmaceutically active ingredient to obtain a pharmaceutical composition.

DETAILED DESCRIPTION OF THE INVENTION

The present invention is now described in more detail by referring to further preferred and further advantageous embodiments and examples, which are however presented for illustrative purposes only and shall not be understood as limiting the scope of the present invention.

According to the present invention, a novel process for the production of moxonidine of formula I or a pharmaceutically acceptable salt thereof is provided.

The starting compound, 4,6-dichloro-2-methyl-5-(1-acyl-2-imidazolin-2-yl)-aminopyrimidine (II), is commercially available for acyl equals acetyl and can be used as received. If desired it may also be prepared by known procedures as described in the literature. The protecting group R (preferably Acyl group, compound of formula IIa) may be selected from formyl, acetyl, propionyl, or butyryl groups, without being limited thereto, and may optionally be substituted, e.g. by a phenyl group. Preferably R is acetyl, thus the starting compound is represented by a compound of formula IIa

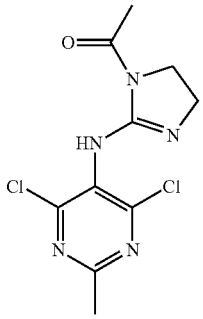

(IIa)

4,6-dichloro-2-methyl-5-(1-acetyl-2-imidazolin-2-yl)-aminopyrimidine (DMAIA).

For conversion, 4,6-dichloro-2-methyl-5-(1-acyl-2-imidazolin-2-yl)-aminopyrimidine II, is mixed with methanol and a non-ionic organic base.

Surprisingly it has been found that reaction can proceed even when employing a non-ionic organic base, i.e. excluding conventional methoxide/methanolate bases and inorganic bases which are associated with disadvantages such as inhomogeneous reaction mixtures that prevent proper control of the reaction and require the subsequent removal of inorganic compounds.

The organic base to be used according to the present invention is preferably selected from organic nitrogen bases and is particularly selected from guanidine group compounds such as N,N,N',N'-tetramethylguanidine and 1-methyl-2,3,4,6,7,8-hexahydro-1H-pyrimido[1,2-a]pyrimidine (N-Methyl-HPP), from amidine group compounds such as 1,5-diazabicyclo[4.3.0]non-5-ene (DBN) and 1,8-diazabicyclo[5.4.0]undec-7-ene (DBU), from the amine group compounds such as n-propylamine iso-propylamine, N-methylcyclohexylamine, dicyclohexylamine, N-methyl-iso-propylamine, N,N-di-iso-propylamine, tert-butylamine, tert-octylamine (2,4,4-trimethylpent-2-ylamine), sec-butylamine and diethylamine, even more preferably guanidine group containing bases and amidines like DBN and DBU, most preferably DBU.

In a preferred embodiment, the ratio of the specified organic base to the key starting material (compound of formula II) is preferably in the range of 1.0-2.0 molar equivalents, more preferably 1.4 to 1.5 molar equivalents of organic base, relative to the starting compound 4,6-dichloro-2-methyl-5-(1-acyl-2-imidazolin-2-yl)-aminopyrimidine (II).

Advantageously, the reaction can be performed in an essentially non-aqueous, organic solvent. The term "essentially non-aqueous" as used herein refers to the amount of water which can be present up to 10 vol %; preferably no water is deliberately added and at most residual water is present in ranges that are typical for technical-grade organic solvents. If another organic medium is optionally present besides methanol, such other solvent medium can be selected from tetrahydrofurane (THF), toluene, dimethyl sulfoxide (DMSO), and mixtures thereof. It is preferred that only methanol is used as the sole reaction medium. Such methanol can be used as it is, without adding water. Also at the end of the reaction, it can be advantageously avoided to mix or quench the reaction medium with water, which was necessary to remove inorganic residuals in the processes known so far. Furthermore, the absence of water allows for a controlled crystallization including a more convenient drying procedure.

In another preferred and optionally combined embodiment, the ratio of methanol to the provided starting compound is particularly adjusted, preferably 20-40 ml and more preferably about 25 ml of methanol is added per g of starting material of formula II.

The reaction is performed at an appropriate temperature, preferably by heating and more preferably by heating to reflux temperature. Furthermore, the reaction is performed during an appropriate reaction period between at least 1 hour and 7 hours. Particularly preferred is reflux for 3 to 4 h.

In another preferred embodiment, activated charcoal is present in the reaction mixture. This effectively removes residual, minute amounts of colouring impurities.

After reaction and prior to crystallisation, an organic acid can be added to the medium, preferably at elevated temperatures (50-65° C.). Any formed "impurity B" (dimethoxy-product) can be retained in the mother liquor. A preferred organic acid is acetic acid.

In a certain aspect of this embodiment, organic acid is applied in quantities required to neutralize the excess of organic base in the reaction mixture and an additional excess of about 0.02-0.15 molar equivalents (relative to the compound of formula II).

In a preferred aspect of this embodiment, acetic acid is added in quantities sufficient to neutralize the excess base plus a small quantity (0.05-0.10 molar equivalents) to provide for a small excess of acid in the reaction mixture.

Thereafter, filtration of the reaction mixture, preferably while still hot, is performed. Moxonidine is obtained from the reaction mixture by gentle cooling, which leads to crystallization of the product.

In another preferred embodiment, the reaction mixture is concentrated e.g. by distillation, optionally and preferably after applying an initial crystallization phase. In a particular aspect of this embodiment, the reaction mixture is concentrated to ⅓ of its initial volume.

In another preferred embodiment, the reaction mixture is cooled to 0° C. before isolation of the product.

In yet another preferred embodiment moxonidine is isolated by filtration or centrifugation.

By this method, the moxonidine product can be readily isolated in high yield and purity. Advantageously, the isolated moxonidine obtained according to the present invention has pharmacopeially acceptable purity, without the need for further purification. Without the drawbacks associated with conventionally used bases and aqueous systems, the process as described herein repeatedly provides an average yield of about 83% and a HPLC purity of greater than 99.5%, while the sum of impurities is not more than 0.25% (Imp. A<0.1%, Imp. B<0.2%).

The moxonidine product as obtained from the process as described above obtained from the reaction virtually as free base. Alternatively it can be converted, directly from the reaction medium or in a subsequent step, into a pharmaceutically acceptable salt.

As to the term "pharmaceutically acceptable salt" used herein, the compound of formula I is in the form of a acid addition salt in which the acid is selected from the group consisting of hydrochloric acid, hydrobromic acid, sulfuric acid, phosphoric acid, glutamic acid, (+)-L-tartaric acid, citric acid, (−)-L-malic acid, DL-lactic acid, L-ascorbic acid, succinic acid, adipic acid, acetic acid, stearic acid, carbonic acid, thiocyanic acid, glycerol-phosphoric acid, L-aspartic acid, maleic acid, fumaric acid, galactaric acid, D-glucuronic acid, glycolic acid, D-glucoheptonic acid, hippuric acid, D-gluconic acid, glutaric acid, sebacic acid, capric (decanoic) acid, lauric acid, palmitic acid, alginic acid, benzoic acid, nicotinic acid, propionic acid, caprylic (octanoic) acid, naphthalene-1,5-disulfonic acid, ethane-1,2-disulfonic acid, cyclamic acid, p-toluenesulfonic acid, methanesulfonic acid, dodecylsulfuric acid, naphthalene-2-sulfonic acid, benzenesulfonic acid, oxalic acid, 2-hydroxy ethanesulfonic acid, ethanesulfonic acid, pamoic (embonic) acid, 2-oxoglutaric acid, 1-hydroxy-2-naphthoic acid, malonic acid, gentisic acid, lactobionic acid, (−)-L-pyroglutamic acid, oleic acid, (+)-camphoric acid, isobutyric acid and orotic acid. Preferably the salt is moxonidine hydrochloride.

According to another aspect of the invention, a pharmaceutical composition is provided, comprising a moxonidine compound of formula I as prepared by the present invention or a pharmaceutically acceptable salt thereof, and then mixed with at least one pharmaceutically acceptable excipient or carrier to obtain said pharmaceutical composition.

The term "pharmaceutically acceptable excipient" as used herein means any physiologically inert, pharmacologically inactive material known in the art being compatible with the physical and chemical characteristics of the active agent. Preferably, the pharmaceutically acceptable excipient is selected from the group consisting of binders, disintegrants, bulk polymers and preservatives.

EXAMPLE

Moxinidine was synthesized from DMAIA according to the following procedure.

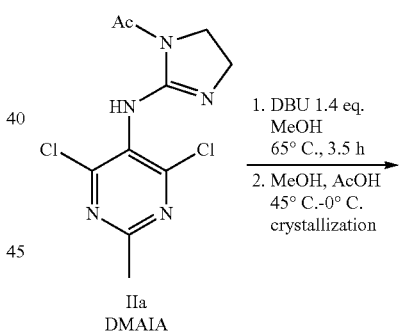

IIa
DMAIA

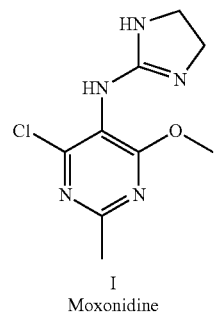

I
Moxonidine

A 4 L glass reactor (with heating jacket) equipped with overhead stirrer, reflux condenser and internal thermometer was charged with DMAIA (149 g, 517 mmol) and activated charcoal (7.50 g). Methanol (3.45 L) and DBU (110 g, 722 mmol, 1.4 eq.) was added and the addition jar rinsed with methanol (100 mL). The jar containing DMAIA was rinsed with methanol (200 mL). The stirrer was turned on and the mixture was heated to reflux (65° C.) for 3.5 h. Then, acetic acid (14.1 g, 234 mmol, 0.45 eq) was added over 7 min. After vacuum filtration of the hot reaction mixture over a paper filter (MN 85/220) and rinsing of the filter cake with hot methanol (100 mL), the filtrate was transferred to a second reactor equipped with overhead stirrer, distillation head with condenser and internal thermometer. The temperature was set to 40-43° C. IT and seeding crystals (1.5 g) were added. A thin suspension formed while the suspension was stirred for 45 min. After further cooling to 20° C. within 1.5 h, the process was discontinued overnight. Then the mixture was concentrated by distillation in vacuo (290 mbar, ET 65° C., IT 37-38° C., dist. temp. 35-37° C., 4.25 h). 2.4 L of solvent were removed. The mixture was cooled to 4° C. within 3 h under stirring and kept at 0-5° C. for 1 h (vacuum was broken at an ET below 36° C.). The suspension was vacuum-filtered (on G4 filter frit) and the reactor rinsed with 450 mL of mother liquor (to collect the remaining product) and the filter cake (product) subsequently washed with cold methanol (120 mL), cold water (2×150 mL) and cold methanol (2×120 mL) to afford a colourless crystalline powder after drying at 60° C. for 19 h (overnight). yield: 106.2 g, 439 mmol, 84.4%. Assay (HPLC): 99.5%, Impurity A<0.05%, impurity B 0.18%, sulphated ash: 0.02%.

The invention claimed is:

1. A process for the synthesis of moxonidine of formula I

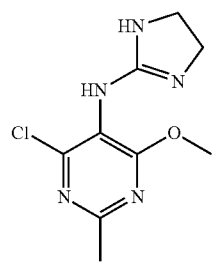

(I)

or a pharmaceutically acceptable salt thereof, the process comprising the steps of:
reacting a 4,6-dichloro-2-methyl-5-(1-acyl-2-imidazolin-2-yl)-aminopyrimidine derivative of formula II

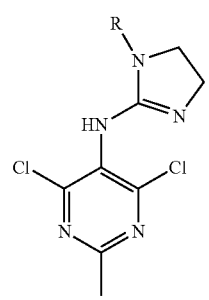

(II)

wherein R denotes an acyl group;
with methanol in the presence of a non-ionic organic base; and
obtaining moxonidine (I) from the reaction mixture.

2. The process according to claim 1, wherein methanol alone is used as the reaction medium, without adding water during or after the completion of the reaction.

3. The process according to claim 1, wherein R is acetyl, i.e. 4,6-dichloro-2-methyl-5-(1-acetyl-2-imidazolin-2-yl)-aminopyrimidine (IIa, R=COCH$_3$) is provided and reacted with methanol.

4. The process according to claim 1, wherein the organic base is selected from organic nitrogen bases.

5. The process according to claim 4, wherein the organic nitrogen base is selected from the group consisting of guanidine group compounds, amidine group compounds and amine group compounds.

6. The process according to claim 5, wherein the organic base is selected from 1,5-diazabicyclo[4.3.0]non-5-ene (DBN) and 1,8-diazabicyclo[5.4.0]undec-7-ene (DBU).

7. The process according to claim 1, wherein 1.0-2.0 molar equivalents of organic base, relative to the provided starting compound 4,6-dichloro-2-methyl-5-(1-acyl-2-imidazolin-2-yl)-aminopyrimidine (II) is used.

8. The process according to claim 1, wherein the ratio of methanol to the provided starting compound is adjusted to 20-40 ml of methanol per g of 4,6-dichloro-2-methyl-5-(1-acyl-2-imidazolin-2-yl)-aminopyrimidine (II).

9. The process according to claim 1, wherein the reaction is carried out in the presence of activated charcoal.

10. The process according to claim 1, wherein prior to obtaining moxonidine from the reaction mixture, organic acid is added.

11. The process according to claim 1, wherein moxonidine is obtained from the reaction mixture by precipitation or crystallization.

12. The process according to claim 1, wherein prior to obtaining moxonidine from the reaction mixture the reaction mixture is concentrated, optionally after an initial crystallization period, and finally moxonidine is isolated.

13. A process for preparing a pharmaceutical composition comprising moxonidine of formula I or a pharmaceutically acceptable salt thereof,

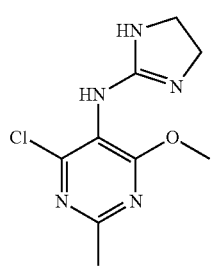

(I)

the process comprising:
carrying out a process according to claim 1 for preparing said moxonidine of formula I or a pharmaceutically acceptable salt thereof, and
mixing the prepared moxonidine compound of Formula I or a pharmaceutically acceptable salt thereof with at least one pharmaceutically active ingredient to obtain a pharmaceutical composition.

14. The process according to claim 10, wherein the organic acid is acetic acid.

* * * * *